United States Patent [19]

Hay

[11] 4,308,865
[45] Jan. 5, 1982

[54] INTERLOCK SYSTEM FOR ANESTHETIC VAPORIZERS

[75] Inventor: Wayne W. Hay, Madison, Wis.

[73] Assignee: Airco, Inc., Montvale, N.J.

[21] Appl. No.: 86,386

[22] Filed: Oct. 19, 1979

[51] Int. Cl.$^3$ .................... A61M 11/00; A61M 17/00
[52] U.S. Cl. .......................... 128/200.14; 128/200.19; 74/483 K
[58] Field of Search ...................... 128/200.11, 200.14, 128/200.16, 200.17, 200.19, 200.21, 203.12, 203.14, 203.25, 203.28, 204.13, 204.14; 261/DIG. 65; 74/483 K, 483 R

[56] References Cited

U.S. PATENT DOCUMENTS

| | | | |
|---|---|---|---|
| 1,090,863 | 3/1914 | Kelley | 128/200.19 X |
| 1,340,930 | 5/1920 | Catlin | 74/483 R |
| 2,646,474 | 7/1953 | Stratton | 74/483 R X |
| 2,756,612 | 7/1956 | Schleicher | 74/483 R X |
| 2,764,182 | 9/1956 | Mitcham | 74/483 R X |
| 3,831,599 | 8/1974 | Needham | 128/203.12 |
| 4,058,120 | 11/1977 | Caparrelli et al. | 128/203.12 |

FOREIGN PATENT DOCUMENTS 255258 11/1912 Fed. Rep. of Germany ........................ 128/200.11
778787 7/1957 United Kingdom ........... 128/203.25
1193522 6/1970 United Kingdom ........... 128/203.28

OTHER PUBLICATIONS

Ohio., Unitrol Anesthesia Machine, Airco Products Catalog Form No. 9906 (Rev. 1978).

Primary Examiner—Henry J. Recla
Attorney, Agent, or Firm—Roger M. Rathbun; Larry R. Cassell

[57] ABSTRACT

A vaporizer interlock system is disclosed which is used in an anesthesia machine having two calibrated vaporizers for providing an anesthetic to a patient and further having a selector valve with three positions, two extreme positions where one of the two vaporizers is being utilized and a middle position where neither vaporizer is used. The system prevents opening of either vaporizer when the selector valve is in the middle position. Also, when the selector valve is moved to one of its extreme positions selecting one of the vaporizers, the other vaporizer is prevented from being moved from its "off" position. The "on" vaporizer must thereafter be placed in its "off" position before the selector valve can be returned to its middle position. In addition, a quick disconnect means is shown for quickly attaching and detaching the vaporizers from the anesthesia machine.

3 Claims, 7 Drawing Figures

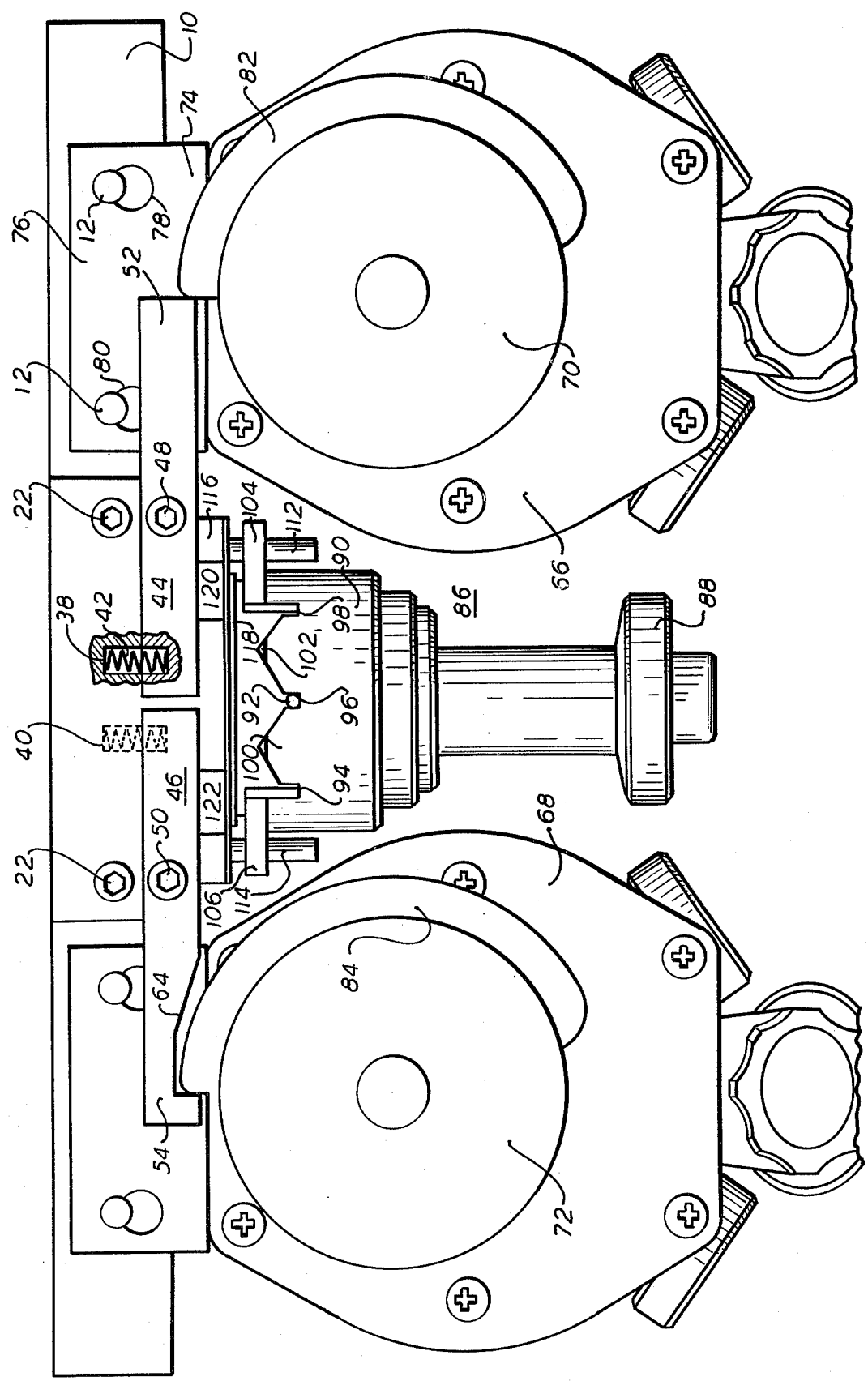

INTERLOCK SYSTEM FOR ANESTHETIC VAPORIZERS

BACKGROUND OF THE INVENTION

This invention relates to an anesthesia machine, and more particularly, to an interlock system for use with two anesthetic vaporizers and which is utilized with a selector valve having three positions, i.e. two extreme positions, where one of the two vaporizers may be used, and a middle position where neither vaporizer can be used. The interlock system prevents the possibility of eithe vaporizer being in the "on" position at any time when that vaporizer has not been selected to supply an anesthetic to a patient.

Anesthesia machines are relatively common in which one or more calibrated vaporizers are used to supply an anesthetic gas to a patient. Each vaporizer supplies a different anesthetic and can be selected by the user in accordance with the particular anesthetic chosen to be utilized.

As a safety measure, it is advantageous to have some system whereby the operator cannot inadvertently turn both vaporizers on at one time, or turn on the wrong vaporizer when, in fact, he has not chosen to use that particular anesthetic.

SUMMARY OF THE INVENTION

The invention comprises an interlock system wherein two calibrated vaporizers are mounted on a manifold of an anesthesia machine and a selector valve is located therebetween. The selector valve has three positions; two extreme positions where one of the two vaporizers may be used and a middle position wherein neither vaporizer can be used.

The system includes a latching ring which rotates with the selector valve and has two recesses. A pair of latches, each pivotable about a point, allows each latch to pivot between a first and a second position. Each latch has one end thereof shaped such as to fit within only one of said two recesses. The latches are biased toward their first position wherein the latches have their shaped ends fitted within their corresponding recess in the latching ring when the latching ring is in the appropriate position. The other end of each of the latches is adapted, when in its second position, to physically prevent opening of one of the vaporizers and can therefore only be in that second position when such vaporizer is in the "off" position.

The latch ring has its recesses positioned such that when the selector valve is in one of its extreme positions, only one of the latches is movable into its first position, thereby allowing one of said vaporizers to be moved from its "off" position, while the other vaporizer must remain in its "off" position.

In the middle position of the selector valve, both latches must be in their second position, that is when both vaporizers must be in their "off" positions and neither can be moved from that off position until the selector valve is moved to one of its extreme positions.

In practice, the selector valve is movable to the right or clockwise towards the vaporizer mounted on the manifold to the right of the selector valve, such that the right hand latch moves to its first position, thereby freeing that vaporizer to be moved to some position other than off. At such time, the left latch cannot move from its second position and thus the left vaporizer must remain in its off position. Thus the user can put either vaporizer in use only by turning the selector valve toward that vaporizer and such vaporizer must thereafter be turned to its off position before the selector valve can be returned to its middle position.

BRIEF DESCRIPTION OF THE DRAWINGS

The invention is diagrammatically illustrated, by way of example, in the drawings appended hereto, in which:

FIG. 2 is a plan view, partly in cross-section, depicting the interlock system with two vaporizers in position;

DESCRIPTION OF PREFERRED EMBODIMENT

Figure 1:
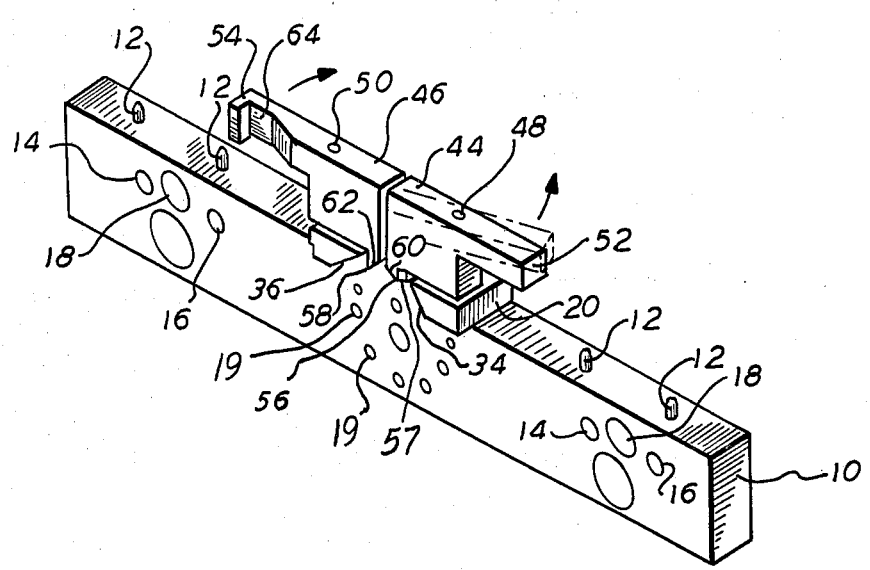
FIG. 1 is an isometric view of the interlock system constructed in accordance with the present invention.

Turning first to FIG. 1, there is shown an isometric view of the interlock system made in accordance with the present invention and used with an anesthesia machine.

As part of the anesthesia machine, only the essential features of such machine needed to describe the present invention being shown, there is a manifold 10 which contains the necessary passageways for gases to be delivered. The passageways themselves are not herein described as they do not form a part of this invention.

The manifold 10 does provide a mounting means for the vaporizers, however, and such means includes two pairs of pins 12 on which two vaporizers are mounted as will be later described. The manifold 10 also includes outlets 14 and inlets 16 which provide gas to and receive anesthetic laden gas from the vaporizers when they are installed on manifold 10. A pair of screw holes 18 are drilled in manifold 10 for use with screws (not shown) that retain the vaporizers securely in position when mounted for use on manifold 10. The afore description applies to positions for mounting a vaporizer on both ends of manifold 10.

In the center of manifold 10, there is a provision for mounting a selector valve to be later described. FIG. 1 shows a plurality of holes 19 that are used to align with and provide gas passageways to such selector valve, however, the particular passageways, again, do not form a part of the present interlock system, except as to denote the particular position where the selector valve is mounted intermediate the mounting positions for the two vaporizers.

Figure 6:
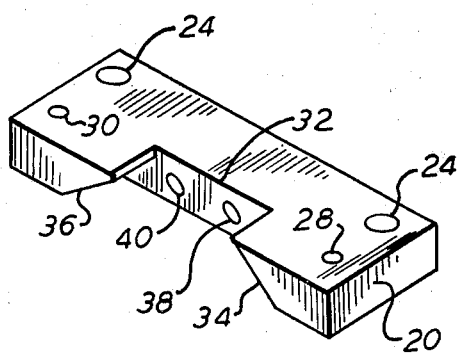
FIG. 6 is an isometric view of a pivot bracket, a component of the present interlock system.
Figure 7:
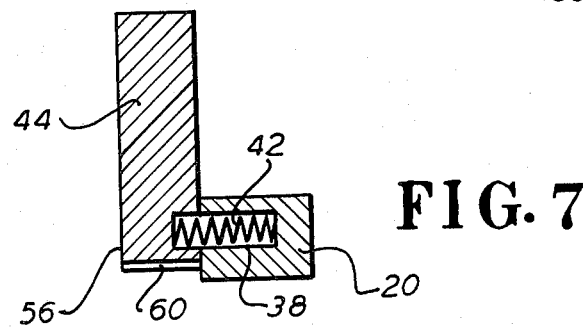
FIG. 7 is an enlarged, cross-sectional view showing a spring biasing means used in the present invention.

On the top of manifold 10, there is mounted a pivot bracket 20, shown also in the isometric FIG. 6. The pivot bracket 20 may be fastened to the manifold 10 by means such as cap screws 22 (shown in FIG. 2) and which pass through holes 24 in the pivot bracket 20. A further set of threaded holes 28 and 30 are formed in the pivot bracket 20 and will be later explained. The pivot bracket 20 has a recessed portion 32 and further has its front surface partially removed as slanted surfaces 34 and 36. A pair of spring holes 38, 40 are formed on the inner surface of the recessed portion 32. As shown in FIG. 7, which is an enlarged cross-sectional view showing the purpose of spring holes 38 and 40, a spring 42 is located in each of the spring holes 38 and 40. Only the spring hole 38 is shown in FIG. 7, however, the functions of the spring holes 38 and 40 are identical.

In both instances the springs 42 exert a bias against latches 44 and 46. As shown in FIG. 1, each of the latches 44 and 46 are pivoted about pivot screws 48, 50 and both latches 44 and 46 have a blocking extension 52 and 54 that extend generally parallel to the manifold 10.

In addition, both of the latches 44 and 46 have, at their other ends, tips 56, 58 which project downwardly and have beveled surfaces 60, 62. One of the latches 46 also includes a recess 64 which affords room for mounting a vaporizer in that position as will be later seen.

The latch 44 is also shown in a dotted line position in FIG. 1 where it has pivoted about its pivot screw 48 to a position in which the blocking extension 52 is displaced counterclockwise about pivot screw 48, moving the blocking extension 52 backwardly, while at the same time moving tip 56 forwardly. The dotted line position is the position toward which spring 42 continually biases the latch 44, and, absent some other constraints preventing such movement, it is the position the latch 44 would normally occupy. It may also be seen that the same biasing is continually applied to latch 46 even though a dotted line position is not illustrated with respect to latch 46.

Turning now to FIG. 2, there is shown a plan view of the interlock system used with a right vaporizer 66 and a left vaporizer 68 screwed in their operational position on manifold 10. In most respects, the vaporizers 66 and 68 operate in conventional manner, however, both are shown in their "off" position. To operate either vaporizer 66 or 68, their control knobs 70 and 72 are rotated counterclockwise from the position shown in FIG. 2.

The vaporizers 66 and 68 are mounted on manifold 10 in a manner such as to provide accurate positioning, yet afford ready connection and disconnections. A vaporizer bracket 74 is L-shaped having one leg thereof affixed to the vaporizer and an outwardly depending leg 76 having two holes 78 and 80. The holes 78 and 80 are each formed of two circular openings of dissimilar diameter slightly overlapped. In mounting the vaporizer 66, the lrger diameter openings are slipped over pins 12 and as the vaporizer 66 is rested against manifold 10 by its own weight, the pins 12 slip into the smaller diameter openings, thereby firmly holding the vaporizer 66 in a cantilever fashion. The same mounting procedure is used with respect to vaporizer 68.

A further feature of the vaporizers 66 and 68 is the presence of locking flanges 82 and 84. In the FIG. 2, each of the locking flanges 82 and 84 are shown engaged by the blocking extensions 52 and 54, respectively, so that the vaporizers 66 and 68, being in their closed positions, cannot have their control knobs 70 and 72 rotated counterclockwise and thus cannot be rotated from the "off" position.

A selector valve 86 is located intermediate the right vaporizer 66 and the left vaporizer 68. The details of the selector valve 86 as to its flow paths and the like do not form part of this invention and hence will not be herein detailed, however, the basic outline of its operation will be described inasmuch as it is adapted to be placed into any one of three operating positions, two extreme positions wherein one of the vaporizers 66 or 68 may be utilized to provide an anesthetic to a patient, and a middle position wherein gas passes through the selector valve 86 directly to a patient and neither of the vaporizers 66 and 68 can be used, both being in their "off" position.

Basically selector valve 86 has a handle 88 and which controls the position of a rotor 90. The rotor 90 is movable to and away from manifold 10 and is spring biased to its position shown in FIG. 2, that is, toward manifold 10. A pin 92, two of which are normally used 180° apart, is adapted to fit within one of the three recesses 94, 96 and 98 formed in rotor 90. Intermediate the recesses 94, 96 and 98 are V-shaped cams 100 and 102.

In FIG. 2, the selector valve 86 is in its middle position where pin 92 is fitted within recess 96. As the handle 88 is pulled away from manifold 10 against the spring bias, the rotor 90 may be turned to either of two extreme positions, one of which is clockwise wherein the pin 92 can fit within recess 94. In such position, where the rotor 90 is moved clockwise to its extreme position to the right, the right vaporizer 66 is placed in the flow of gas to a patient and thus, when opened, is operative. Similarly, rotor 90 can be turned to its extreme left position, where pin 92 fits within recess 98, thereby enabling the left vaporizer 68 to be used to provide anesthetic to the patient.

Depending outwardly from rotor 90 are a pair of ears 104, 106 (seen in FIGS. 2 and 3) each of which have holes 108, 110. In sliding engagement within holes 108 and 110, are pins 112 and 114, respectively, and which pins 112 and 114 depend outwardly from a latching ring 116. The latching ring 116 is held in close proximity to the manifold 10 by means of retaining ring 118. Accordingly, as the rotor 90 is moved laterally away from the manifold 10 to rotate the rotor 90 to another selected position, ears 104 and 106 move along pins 112 and 114 such that the latching ring 116 does not move laterally with rotor 90, but does rotate therewith as rotor 90 rotates.

Figure 5:
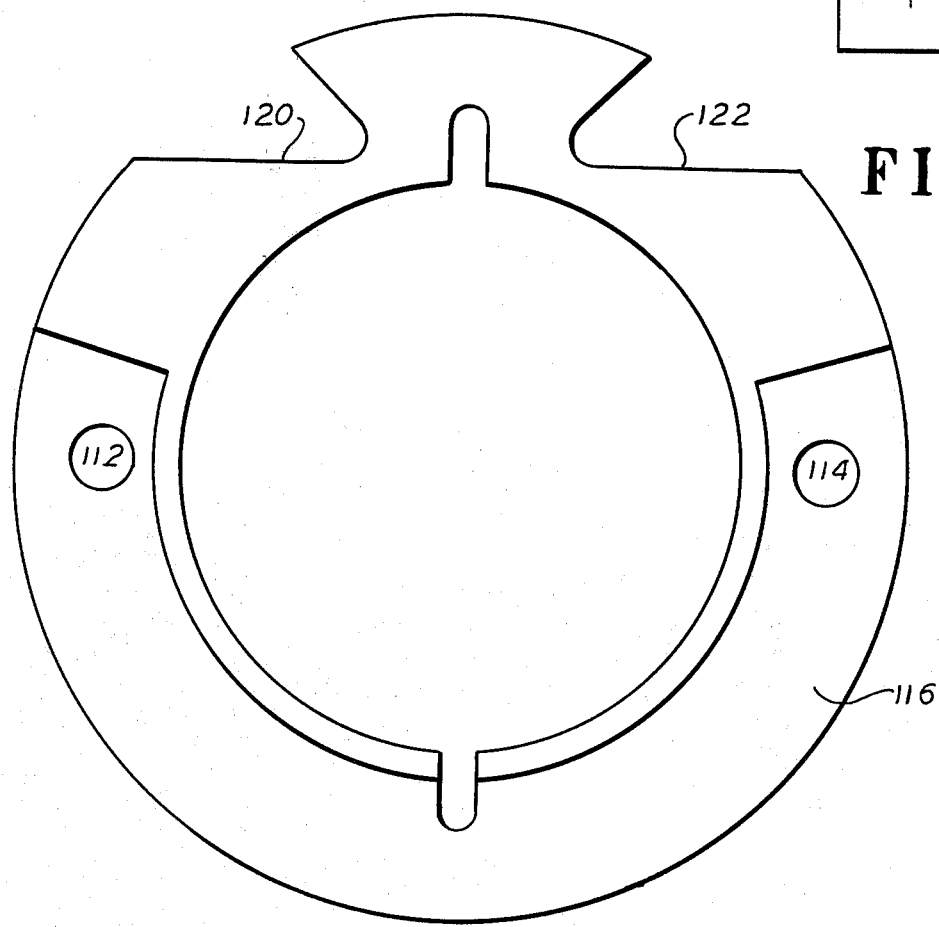
FIG. 5 is a front view of a latching ring, one of the components of the present interlock system.

In FIG. 5, there is a view of the face of the latching ring 116 that faces the manifold 10. The latching ring 116 has a pair of grooves seen viewing the manifold 10 from the front and identified as right groove 120 and left groove 122 and which are cut into the surface of the latching ring 116, and are specially designed such that only tip 56 of latch 44 fits into left groove 122 and only tip 58 of latch 46 can fit within right groove 120 of latching 116 when such latch is aligned with the corresponding groove.

Figure 3:
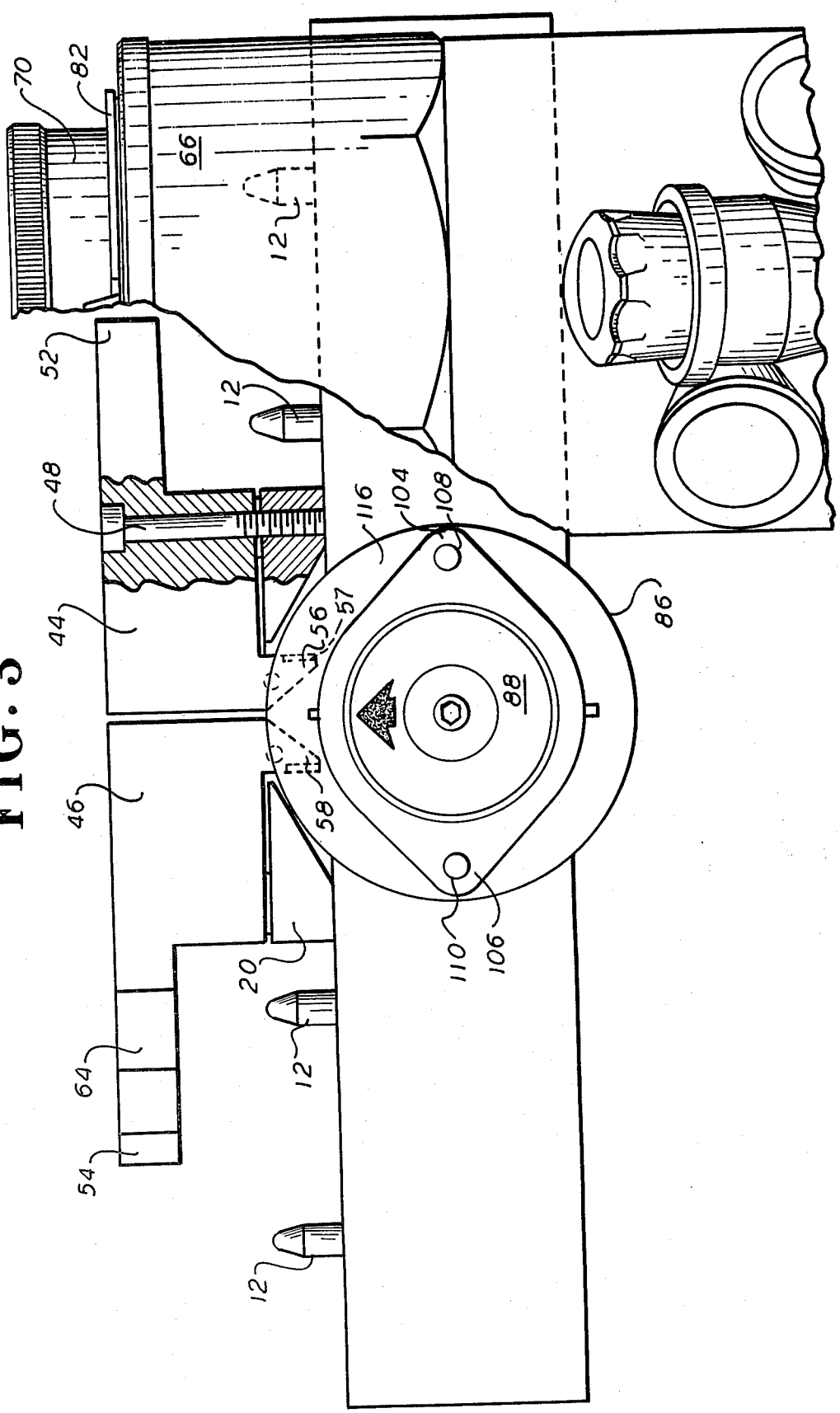
FIG. 3 is a front view, partly in section, and showing one vaporizer partly cut away.

In operation, therefore, again taking FIGS. 2 and 3, in the middle position of selector valve 86, neither of the tips 56 and 58 are in alignment with either of the right groove 120 or left groove 122 and therefore the latches 44 and 46 cannot be pivoted from their position as shown. In such position, both the right vaporizer 66 and the left vaporizer 68 must be in the closed position and their control knobs 70 and 72 cannot be rotated to the open position, since blocking extensions 52 and 54 prevent such movement by blocking, respectively, locking flanges 82 and 84.

In the event an operator desires to utilize the right vaporizer 66, the selector valve handle 88 is turned to the right, clockwise. As the handle 88 turns, latching ring 116 moves correspondingly until the left groove 122 reaches a position in alignment with the latch 44. Since latch 44 can enter left groove 122, it pivots about pivot screw 48 whereby its tip 56 enters left groove 122. The latch 44 moves to its dotted line position of FIG. 1, thereby freeing the blocking extension 52 from its position impeding movement of control knob 70 of the right vaporizer 66. The right vaporizer 66 can therefore be opened for use, yet latch 46 cannot move from its position blocking movement of the control knob 72 of the left vaporizer 68 and therefore such vaporizer must remain in the "off" position.

When the operator no longer desires to use the right vaporizer 66 and therefore intends to move the rotor 90 of selector valve 86 back to its middle position, the tip 56 cannot be removed from the left groove 122, it being held firmly within groove 122 by latch 44 since the blocking extension 52 rides on the outside surface of locking flange 82. The right vaporizer 66 must, therefore, be turned to the closed position, as shown in FIG. 2, before the selector valve 86 can again be returned to its middle position. When right vaporizer 66 is in the closed position, the latch 44 has its tip 56 held in left groove 122 only by means of the bias of spring 42 and by providing a slight beveled surface 57 on the latch tip 56, (FIG. 1) the edge of the left groove 122 forces the beveled surface 57 against the spring bias and the selector valve 86 can be turned to the middle position.

Obviously, the locking action has been described with respect to closing the right vaporizer 66, however, it may readily be seen that the same locking feature is provided with respect to selection of the left vaporizer 68.

Figure 4:
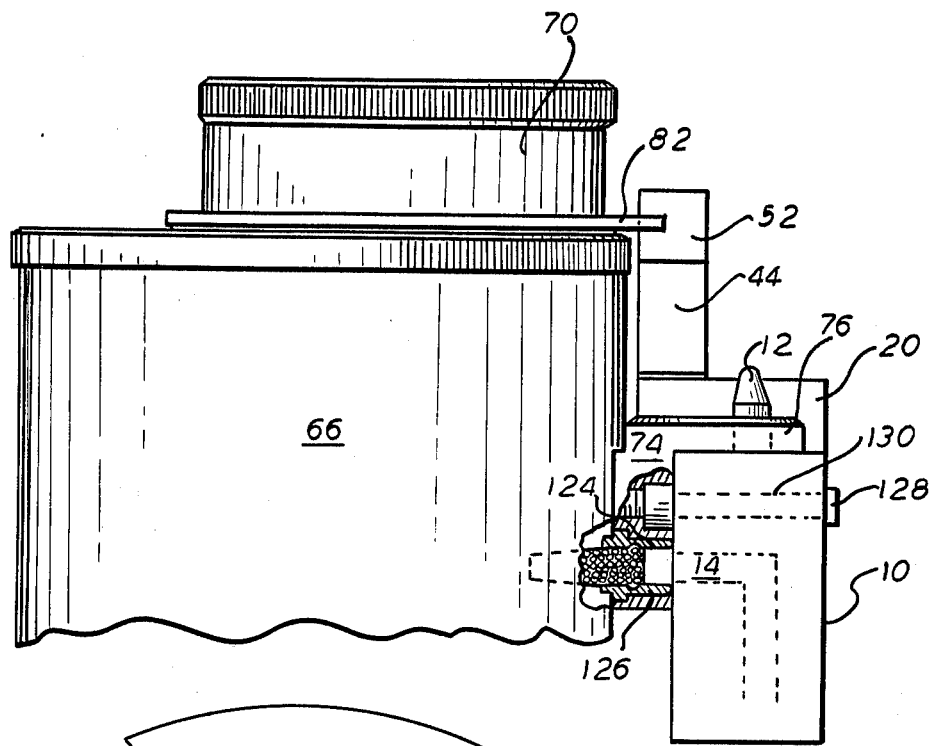
FIG. 4 is a side view, partly in section, showing the quick disconnect means for retaining a vaporizer.

In FIG. 4, a side view is provided showing a profile of an engagement between the locking flange 82 and the blocking extension 52 of latch 44.

In addition, FIG. 4 shows the quick connect and disconnect mounting means for the right vaporizer 66. As seen in FIG. 4, the right vaporizer 66 is hung from pins 12 which insert into the outwardly depending leg 76 of the vaporizer bracket 74. In such position, the right vaporizer 66 hangs cantilever fashion and its weight forces its inlet and outlet, only one of which is shown in the figure as vaporizer inlet 124 against the corresponding opening (outlet 14 as seen in FIG. 1) in manifold 10. A flexible grommet 126 in the vaporizer inlet 124 seals against manifold 10, thus providing a sealed passageway for gas to pass to and from the manifold 10. The right vaporizer 66 can further be held in position by cap screw 128 fitted through a corresponding hole 130 in manifold 10 and threaded into internal threads in the vaporizer bracket 74.

Thus, only one cap screw 128 holds the right vaporizer 66 in its position upon manifold 10 and the weight of the vaporizer forms sealed passageways for gas to flow from the manifold 10 to the vaporizer inlet 124 and return to the manifold 10 through vaporizer outlet (not shown).

It will be understood that the scope of the method and product of this invention is not limited to the particular steps or materials disclosed herein, by way of example, but only by the scope of the appended claims.

I claim:

1. An anesthesia machine having an interlock system, said anesthesia machine comprising a manifold, first and second anesthetic vaporizers mounted on said manifold, each of the vaporizers including control means rotatable to open and closed positions, a selector valve mounted on said manifold intermediate the first and second vaporizers, said selector valve having first and second extreme position wherein said first and second vaporizers, respectively, are operable, and said selector valve having a middle position wherein neither of said first and second vaporizers is operable, said interlock system mounted on said manifold and comprising means to prevent rotation of said control means toward the open position of the first vaporizer when said selector valve is in said second extreme position, and to prevent rotation of said control means toward the open position of said second vaporizer when said selector valve is in said first position and to prevent rotation of both control means of said first and second vaporizers toward the open positions when said selector valve is in said middle position.

2. An anesthesia machine as defined in claim 1 wherein said means to prevent opening of said first and second vaporizers comprises two pivotable latch means, each having first and second positions and each adapted to physically block, when in their second position, rotation of one of said control means of said first and second vaporizers and said interlock system further includes means to allow and prevent movement of said pivotable latches to the first and second positions.

3. An anesthesia machine as defined in claim 2 wherein both of said pivotable latches are biased toward their first position, and said means to allow and prevent movement of said pivotable latches to the first and second positions comprises a latching ring movable with said selector valve and having two recesses, each of said latches being movable individually to its first position when said latch is aligned by movement of said selector valve in predetermined position with respect to one of said two recesses such that said latch enters said aligned recess.

* * * * *